(12) United States Patent
Barnard

(10) Patent No.: US 12,409,041 B2
(45) Date of Patent: Sep. 9, 2025

(54) DEVICE AND METHOD FOR ACROMION REPLACEMENT

(71) Applicant: Exactech, Inc., Gainesville, FL (US)

(72) Inventor: Brian Barnard, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 988 days.

(21) Appl. No.: 17/442,970

(22) PCT Filed: Mar. 27, 2020

(86) PCT No.: PCT/US2020/025402
§ 371 (c)(1),
(2) Date: Sep. 24, 2021

(87) PCT Pub. No.: WO2020/198651
PCT Pub. Date: Oct. 1, 2020

(65) Prior Publication Data
US 2022/0192837 A1    Jun. 23, 2022

Related U.S. Application Data

(60) Provisional application No. 62/824,871, filed on Mar. 27, 2019.

(51) Int. Cl.
*A61F 2/40* (2006.01)
*A61F 2/30* (2006.01)

(52) U.S. Cl.
CPC ...... *A61F 2/40* (2013.01); *A61F 2002/30433* (2013.01); *A61F 2002/30535* (2013.01); *A61F 2002/4088* (2013.01)

(58) Field of Classification Search
CPC ............ A61F 2/3099; A61F 2/40; A61F 2002/30995; A61F 2002/30996; A61F 2002/30998; A61F 2002/4088
See application file for complete search history.

(56) References Cited

U.S. PATENT DOCUMENTS

| | | |
|---|---|---|
| 2005/0154469 A1 | 7/2005 | Novelli |
| 2014/0296987 A1 | 10/2014 | Shohat |

FOREIGN PATENT DOCUMENTS

| | | |
|---|---|---|
| CN | 202568418 U | 12/2012 |
| CN | 204364103 U | 6/2015 |
| WO | 2018/026785 A1 | 2/2018 |

OTHER PUBLICATIONS

International Search Report and Written Opinion from International Appln. No. PCT/US2020/025402 dated Jul. 15, 2020.

*Primary Examiner* — Marcia L Watkins
(74) *Attorney, Agent, or Firm* — GREENBERG TRAURIG, LLP

(57) ABSTRACT

A device includes an acromion portion sized and shaped to replicate functions of the native acromion, and a fixation portion connected to the acromion portion, the fixation portion including a first arm portion and a second arm portion spaced apart from the first arm portion, wherein the first arm and second arm portions are positioned such that, when the device is positioned such that the acromion portion is in a native position of the absent native acromion, the first arm portion overlays a superior face of a scapular spine of the scapula and the second arm portion overlays an inferior space of the scapular spine of the scapula, wherein each of the first arm portion and the second arm portion includes at least one screw fixation point extending therethrough and configured to receive a screw therein so as to secure the device to the scapula.

22 Claims, 10 Drawing Sheets

Figure 3G
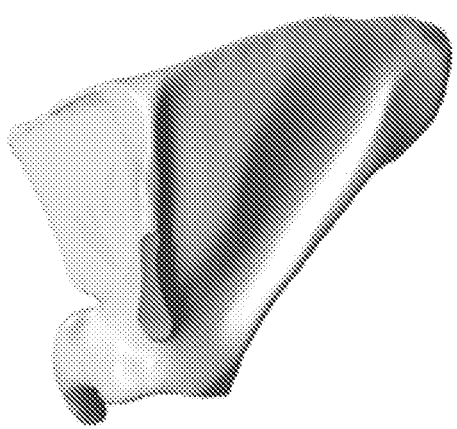
Figure 3H
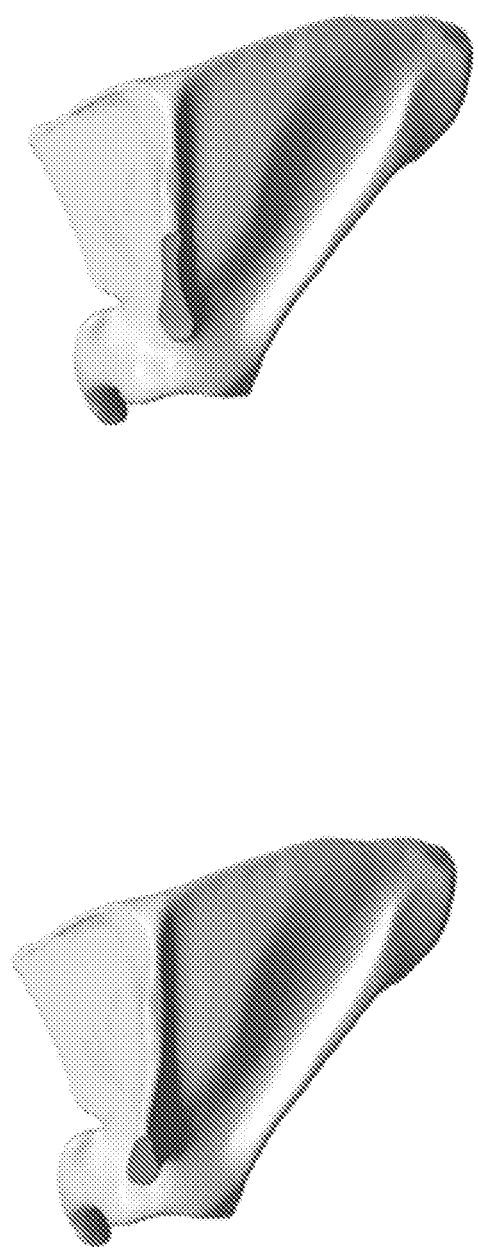
Figure 3E
Figure 3F

DEVICE AND METHOD FOR ACROMION REPLACEMENT

CROSS-REFERENCE TO RELATED APPLICATION

This is an international (PCT) application relating to and claiming the benefit of commonly-owned, co-pending U.S. Provisional Patent Application No. 62/824,871, entitled "DEVICE FOR ACROMION REPLACEMENT," filed Mar. 27, 2019, the contents of which are incorporated herein by reference in their entirety.

FIELD OF THE INVENTION

The field of invention relates to devices for orthopedic use. More particularly, the field of invention relates to devices for use in the reconstruction of fatigue/insufficiency factures of the acromion and scapula that can occur after reverse total shoulder arthroplasty.

BACKGROUND OF THE INVENTION

Reverse total shoulder arthroplasty ("rTSA") is a surgical technique in which the shoulder's natural ball-and-socket joint, which has a rounded humeral head (i.e., ball) interfacing with the glenoid cavity (i.e., socket) of the scapula, is replaced by a reversed ball-and-socket joint, which has a glenosphere (i.e., ball) implanted on the glenoid cavity of the scapula and mating with a cup (i.e., socket) implanted on the humerus. Occasionally, fatigue/insufficiency fractures occur in the acromion and scapula after rTSA. Reconstruction of acromial and scapula fatigue/insufficiency fractures after rTSA is a challenging and unsolved problem. These fracture types are not always able to be repaired; and healing after repair is not always reproducible for even the best shoulder specialists and traumatologists due to the highly variable anatomy which often consists of relatively thin bone with low vascularity. Generally, there are only a few currently available solutions for open reduction and internal fixation ("ORIF") surgery. When ORIF is used, shoulder specialists and traumatologists primarily utilize one or more straight/noncontoured plates with locking screws, compression screws, and/or a combination of each. Because of the highly variable scapular anatomy in terms of both size and shape/contour, few anatomically contoured plates are available and surgeons are often required to bend straight plates in order to get a better fit. Due to concerns of repair and healing, one method of treatment is immobilization of the patient's arm in a sling until the fracture heals. For both ORIF and immobilization, the rate of healing is unpredictable. FIG. 1 shows a representative radiographic depiction of a scapular fracture after rTSA.

Recently, rTSA outcome studies have demonstrated that even if a fatigue/insufficiency fracture heals, the patient will not achieve the level of outcome and function that they experienced prior to the fracture. If the fracture fails to heal, the results are poor as the middle deltoid origin is on the acromion and the posterior deltoid origin is on the lateral acromion and scapular spine. Without proper deltoid function, the reverse shoulder prosthesis fails to be able to generate a torque necessary for activities of daily living and also joint stability is impaired.

Acromial and scapula fatigue/insufficiency fractures can generally occur anytime after the initial rTSA procedure, occurring as early as the first day of surgery and as late as 10+ years after the surgical procedure. Acromial and scapula fatigue/insufficiency fractures after rTSA can occur at various locations on the acromion and scapular spine. (FIG. 2) These fracture types have been recently classified as type 1 (fracture of the lateral acromion with a deltoid avulsion), type 2 (fracture of the mid-scapular spine at-or around the location of the scapular notch), and type 3 (fracture at the base of the scapular spine). (FIG. 3) The rate of acromial and scapula fatigue/insufficiency fractures after rTSA is relatively low, but is typically reported to be between 1 and 10%. Type 2 fractures appear to be the most common scapular insufficiency fracture type after rTSA.

There are numerous potential causes of these acromial and scapular insufficiency/fatigue fractures. One potential cause is that the fracture propagates from the tip of the glenoid baseplate screw into the scapular spine. Another potential cause is that the fractures occur due to overactivity or episodes of strenuous activity and/or trauma. Another potential cause is that the fracture is caused by over-tensioning the deltoid and/or arm lengthening as a function of overstuffing the joint with too thick of an implant or too distal of an implant configuration for a given patient's anatomy. Other potential causes include the use of biomechanically inefficient implants which have too small of a deltoid moment arm (resulting in too great of a deltoid force for arm elevation for a particular patient). There are also likely patient-specific anatomic/morphologic factors which predispose the patient to these types of insufficiency fractures, like a thin scapula/acromion, osteoporotic or osteopenic bone, the presence of an Os acromiale or a lesion which is associated with Cuff Tear Arthropothy ("CTA") pathology, or perhaps a unique biomechanically detrimental anatomy such that there is insufficient acromial overhang or muscle mass, requiring the patient to produce abnormal physiologic loading during activities of daily loading. rTSA patients are associated with more scapular motion relative to non-rTSA patients, and it may be that the amount of scapular rotation influences this complication. The timing and level of rigor of the rehabilitation program may also play a role on the rate and severity of the acromial or scapular fatigue/insufficiency fracture. These fractures could also be caused during the surgery by traction with a retractor when attempting to gain exposure to the glenoid. Whatever the specific cause (or combination of causes), the patient population is predominantly female, osteoporotic, and elderly. As a result of these factors, the fracture is at a disadvantage for healing. Patient health quality and patient co-morbidities also influence the quality of fracture reconstruction and the rate and probability of fracture healing over time.

The widespread and global usage of rTSA since its clearance in the US in 2003 and the lack of consensus solution to this complication type highlights the need for a better solution for acromial/scapular insufficiency fractures after rTSA, but also highlights the need for a solution if that fracture reconstruction fails, which has been reported at a relatively high rate due to patient factors and anatomic factors. For all these reasons, there is a need for a more effective solution to restore function and stability to the rTSA after an acromial/scapular insufficiency fatigue fracture.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 3E shows a superior view of a scapula after a Type 2 fracture;

FIG. 3F shows a posterior view of the fractured scapula shown in FIG. 3E;

FIG. 3G shows a superior view of a scapula after a Type 3 fracture;

FIG. 3H shows a posterior view of the fractured scapula shown in FIG. 3G;

SUMMARY OF THE INVENTION

Figures 1A, 1B:
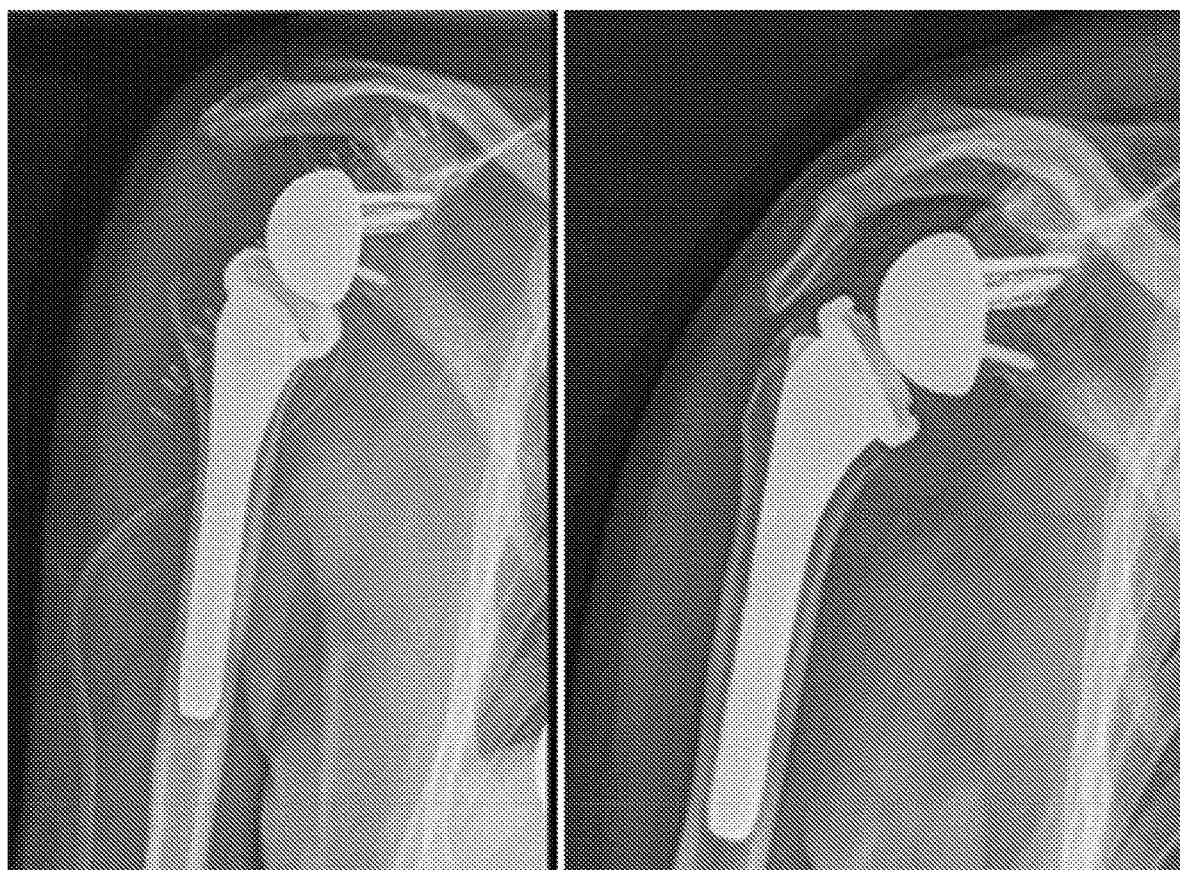
FIG. 1A shows an anterior-posterior radiographic view of a shoulder joint after rTSA and prior to scapular fracture.
FIG. 1B shows the rTSA shoulder joint of FIG. 1A after scapular fracture.
Figure 2A:
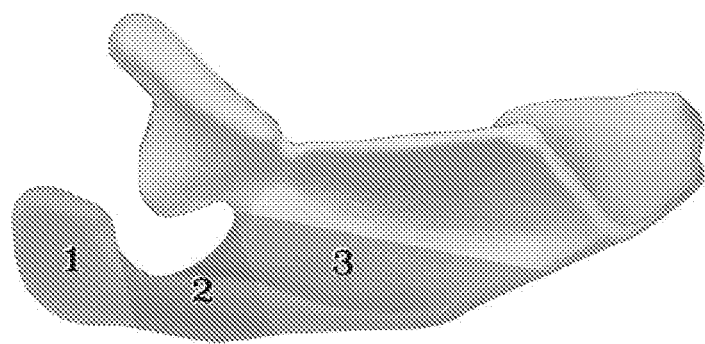
FIG. 2A shows a superior view of the locations of different scapular fractures.
Figure 2B:
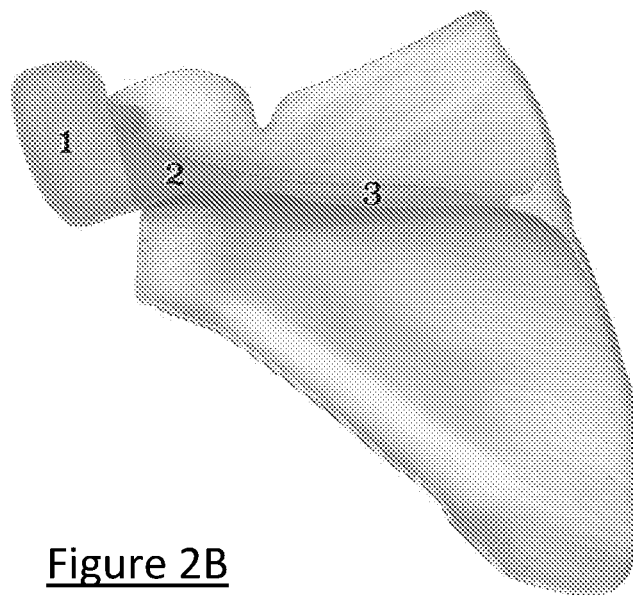
FIG. 2B shows a posterior view of the scapular fractures shown in FIG. 2A.
Figure 2C:
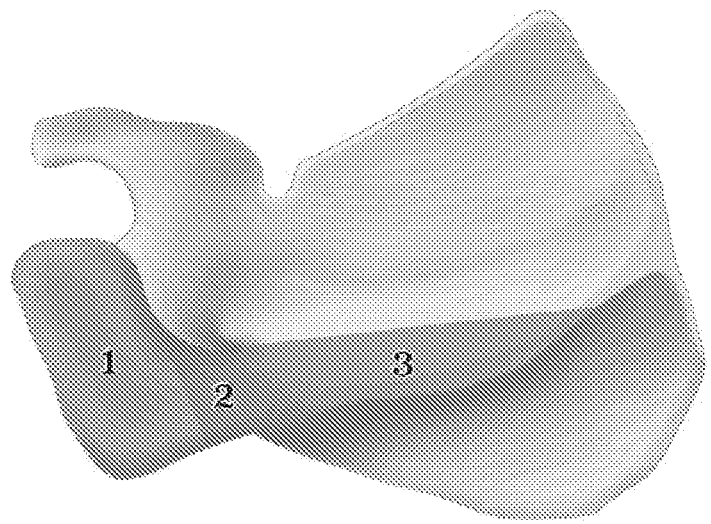
FIG. 2C shows a superior-oblique view of the scapular fractures shown in FIG. 2A.

The exemplary embodiments relate to devices for repair of acromial/scapular fractures. In some embodiments, the devices described herein are suitable for use as an end stage acromial/scapular reconstruction/replacement implant for patients who have unrepairable insufficiency fractures of the acromion or scapula, who either have a failed reconstruction of the acromion or scapula, or for patients who have had a nonunion or malunion of the acromial/scapula fracture.

In an embodiment, an acromion replacement device configured for repair of a scapular fracture in a patient includes a mounting portion and an acromion portion, the mounting portion including a first arm configured to be positioned to a first side of a scapular spine of the patient and configured to receive a fixation element to thereby fix the first arm to the first side of the scapular spine of the patient, the mounting portion further including a second arm configured to be positioned to a second side of the scapular spine of the patient and configured to receive a fixation element to thereby fix the second arm to the second side of the scapular spine of the patient, the acromion portion being sized, shaped, and positioned to replicate a native acromion of the patient when the first and second arms are fixed to the scapular spine of the patient.

In some embodiments, a device that is configured to replace an absent native acromion of a scapula of a patient includes an acromion portion sufficiently sized and shaped to replicate functions of the native acromion, and a fixation portion connected to the acromion portion, the fixation portion including a first arm portion and a second arm portion spaced apart from the first arm portion, wherein the first arm portion is positioned with respect to the acromion portion such that, when the device is positioned adjacent to the scapula such that the acromion portion is in a native position of the absent native acromion, the first arm portion overlays a superior face of a scapular spine of the scapula, and wherein the second arm portion is spaced apart from the first arm portion such that, when the device is positioned such that the first arm portion overlays the superior face of the scapular spine of the scapula, the second arm portion overlays an inferior space of the scapular spine of the scapula, wherein each of the first arm portion and the second arm portion includes at least one screw fixation point extending therethrough, wherein each of the at least one screw fixation point is configured to receive a screw therein so as to secure the device to the scapula.

In some embodiments, the fixation portion also includes a middle portion connecting the acromion portion to the first arm portion and to the second arm portion, wherein the middle portion is positioned such that, when the device is positioned such that the first arm portion overlays the superior face of the scapular spine of the scapula, the middle portion overlays a crest of the scapular spine of the scapula. In some embodiments, the middle portion includes at least one screw fixation point extending therethrough.

In some embodiments, the acromion portion includes at least one soft tissue attachment point. In some embodiments, the acromion portion includes an array of soft tissue attachment points. In some embodiments, each of the at least one soft tissue attachment point has a size in a range of from 5 mm to 50 mm.

In some embodiments, each of the first arm portion and the second arm portion includes a plurality of the screw fixation points. In some embodiments, the screw fixation points are arranged in at least one row. In some embodiments, the screw fixation points are arranged in a triangle. In some embodiments, a spacing distance between adjacent ones of the plurality of screw fixation points is between 1 centimeter and 4 centimeters.

In some embodiments, the device also includes at least one extension extending away from either the first arm portion, the second arm portion, or both, wherein each of the at least one extension includes at least one screw fixation point extending therethrough. In some embodiments, at least one of the at least one extension extends away from either the first arm portion or the second arm portion at an end of the first arm portion or the second arm portion that is closest to the acromion portion. In some embodiments, at least one of the at least one extension extends away from either the first arm portion or the second arm portion at an end of the first arm portion or the second arm portion that is furthest from the acromion portion. In some embodiments, the at least one extension is modularly attached to and removable from the device.

In some embodiments, the device is integrally formed. In some embodiments, the device includes a biocompatible material. In some embodiments, the biocompatible material includes a cobalt-chromium alloy, stainless steel, titanium, a titanium alloy, a nickel-titanium alloy, a polymer, a reinforced polymer, a carbon fiber-reinforced polymer, a glass-reinforced polymer, a non-reinforced polymer, a ceramic, a polymethyl-methacrylate, bone cement, pyrocarbon, bone graft, or a combination thereof.

In some embodiments, the acromion portion is sized and shaped to replace an absent acromion of a scapula that has experienced either a type 1 fracture, a type 2 fracture, or a type 3 fracture.

In some embodiments, the acromion portion is sized and shaped to replicate a size and shape of the native acromion.

In some embodiments, each of the at least one screw fixation point includes either a screw hole, a screw slot, or a compression slotted hole.

In some embodiments, a method includes providing a device that is configured to replace an absent native acromion of a scapula of a patient, and which includes an acromion portion sufficiently sized and shaped to replicate functions of the native acromion, and a fixation portion connected to the acromion portion, the fixation portion including a first arm portion and a second arm portion spaced apart from the first arm portion, wherein the first arm portion is positioned with respect to the acromion portion such that, when the device is positioned adjacent to the scapula such that the acromion portion is in a native position of the absent native acromion, the first arm portion overlays a superior face of a scapular spine of the scapula, and wherein the second arm portion is spaced apart from the first arm portion such that, when the device is positioned such that the first arm portion overlays the superior face of the scapular spine of the scapula, the second arm portion overlays an inferior space of the scapular spine of the scapula, wherein each of the first arm portion and the second arm portion includes at least one screw fixation point extending therethrough, wherein each of the at least one screw fixation point is configured to receive a screw therein so as to secure the device to the scapula; positioning the device adjacent to a scapula of a patient that has experienced a fracture of the scapula causing the native acromion to be absent, such that the acromion portion of the device is positioned in a position that would be occupied by the native acromion; and securing the device to the scapula by inserting at least one screw through the screw holes of the device and into the scapula.

In some embodiments, the acromion portion of the device includes at least one soft tissue attachment point, and wherein the method also includes securing at least one of a deltoid of the patient or a trapezius of the patient to at least one of the at least one soft tissue attachment point.

DETAILED DESCRIPTION OF THE INVENTION

Figure 4A:
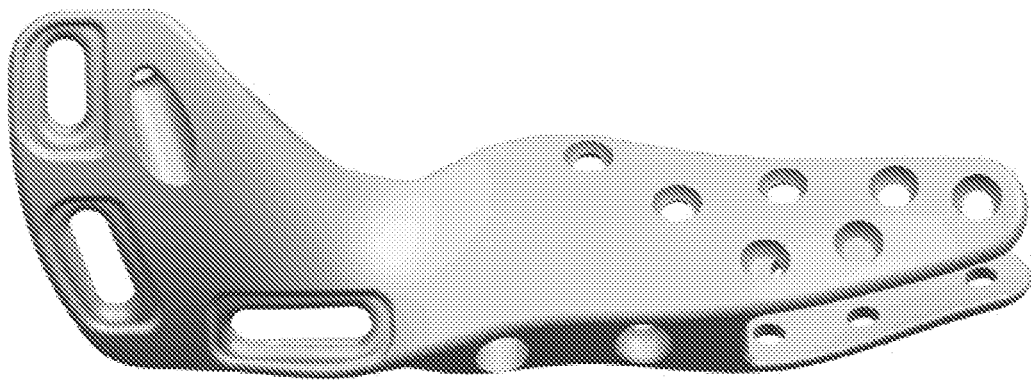
FIG. 4A shows a superior-oblique view of a first exemplary embodiment of a scapular replacement device.
Figure 4B:
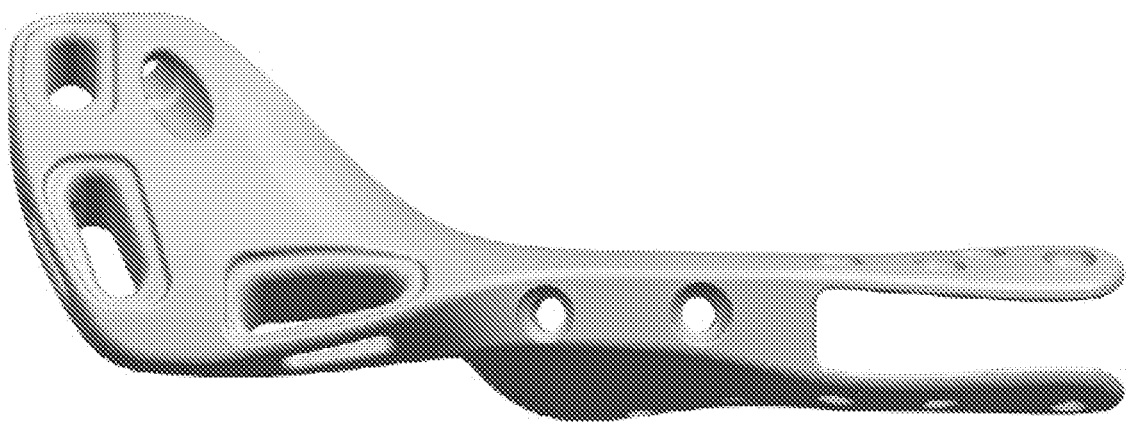
FIG. 4B shows a posterior view of the exemplary scapular replacement device of FIG. 4A.
Figure 4C:
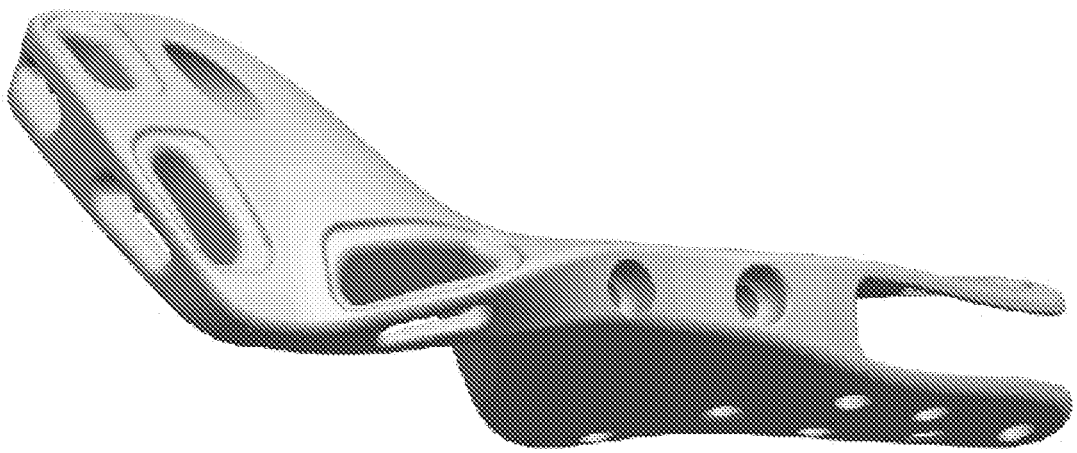
FIG. 4C shows an inferior-oblique view of the exemplary scapular replacement device of FIG. 4A.
Figure 5B:
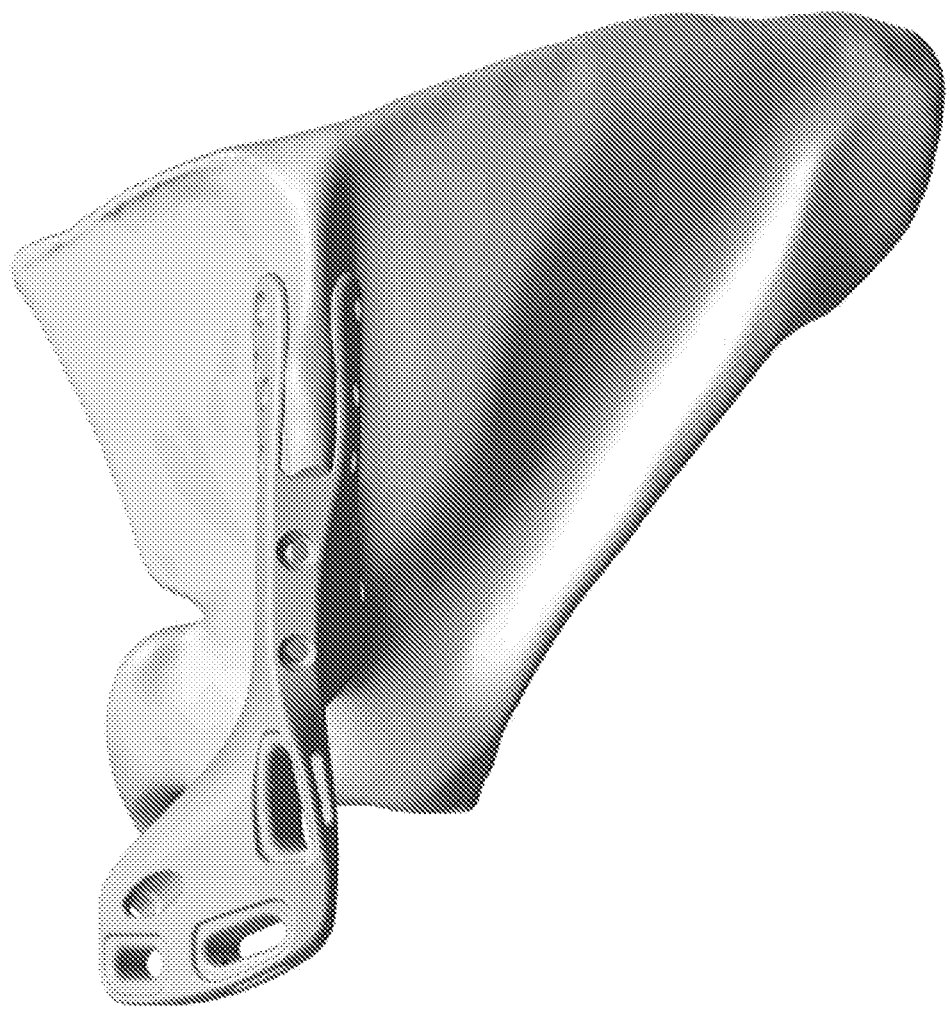
FIG. 5B shows a posterior view of the exemplary scapular replacement device and representative scapula of FIG. 5A.
Figure 5A:
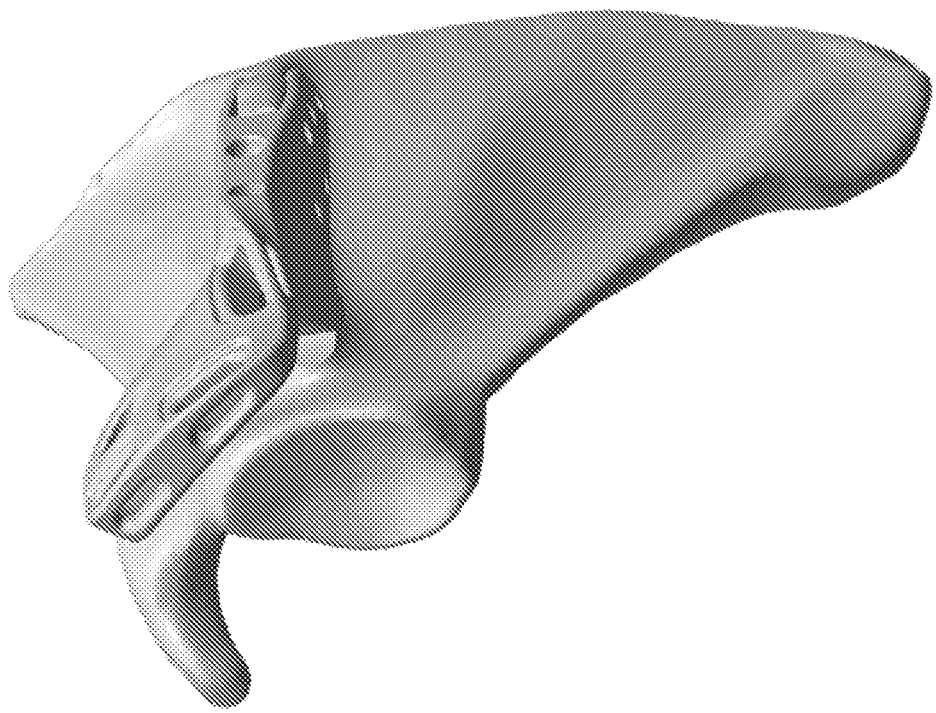
FIG. 5A shows a lateral-oblique view of the exemplary scapular replacement device of FIG. 4A as fixed to a representative scapula.
Figure 6A:
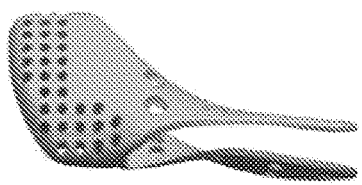
FIG. 6A shows a posterior view of a second exemplary embodiment of a scapular replacement device.
Figure 6B:
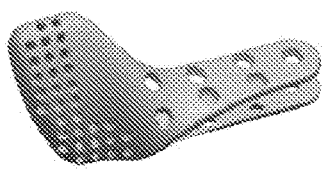
FIG. 6B shows a superior-oblique view of the exemplary scapular replacement device of FIG. 6A.
Figure 6C:
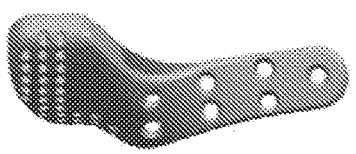
FIG. 6C shows a superior view of the exemplary scapular replacement device of FIG. 6A.
Figure 6D:
FIG. 6D shows an inferior view of the exemplary scapular replacement device of FIG. 6A.
Figure 7A:
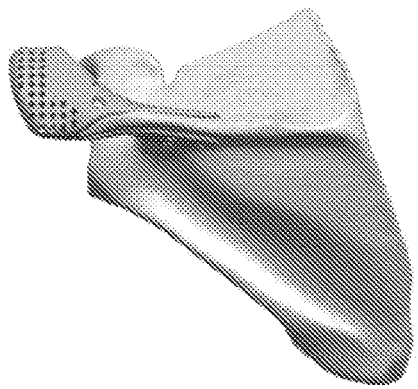
FIG. 7A shows a posterior view of the exemplary scapular replacement device of FIG. 6A as fixed to a representative scapula.
Figure 7B:
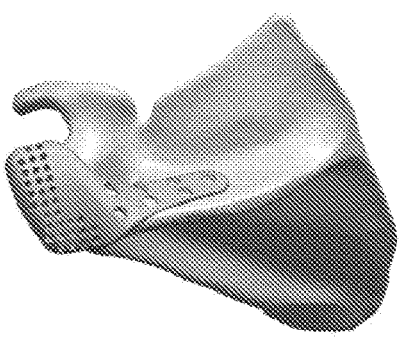
FIG. 7B shows a superior-oblique view of the exemplary scapular replacement device of FIG. 6A as fixed to a representative scapula.
Figure 7C:
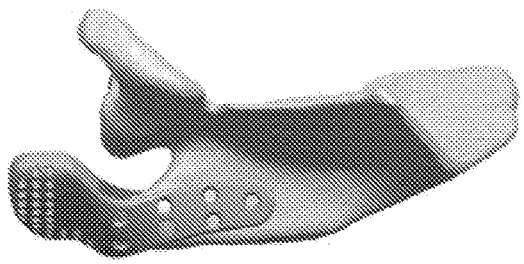
FIG. 7C shows a superior view of the exemplary scapular replacement device of FIG. 6A as fixed to a representative scapula.
Figure 7D:
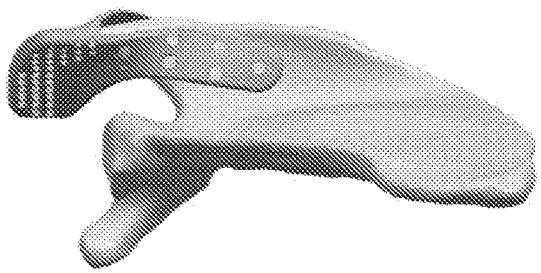
FIG. 7D shows an inferior view of the exemplary scapular replacement device of FIG. 6A as fixed to a representative scapula.
Figure 8A:
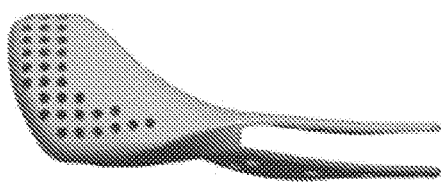
FIG. 8A shows a posterior view of a third exemplary embodiment of a scapular replacement device.
Figure 8B:
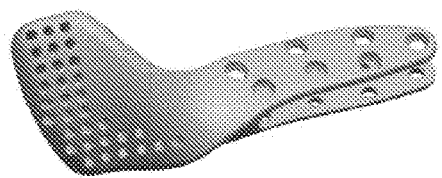
FIG. 8B shows a superior-oblique view of the exemplary scapular replacement device of FIG. 8A.
Figure 8C:
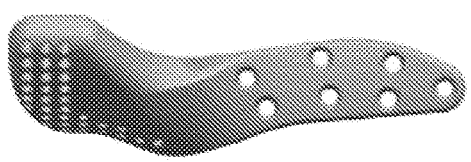
FIG. 8C shows a superior view of the exemplary scapular replacement device of FIG. 8A.
Figure 8D:
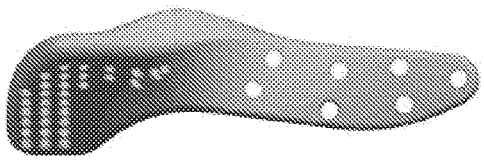
FIG. 8D shows an inferior view of the exemplary scapular replacement device of FIG. 8A.
Figure 9A:
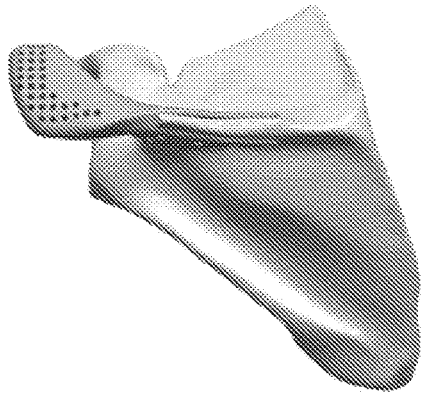
FIG. 9A shows a posterior view of the exemplary scapular replacement device of FIG. 8A as fixed to a representative scapula.
Figure 9B:
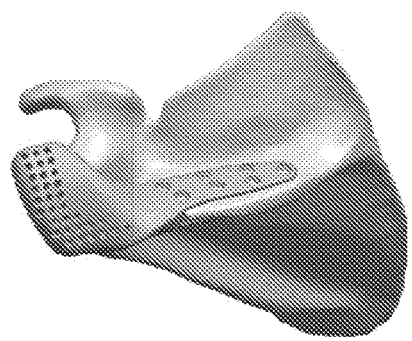
FIG. 9B shows a superior-oblique view of the exemplary scapular replacement device of FIG. 8A as fixed to a representative scapula.
Figure 9C:
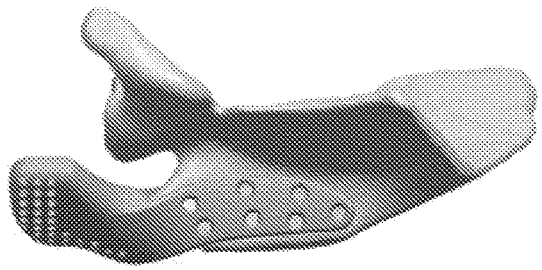
FIG. 9C shows a superior view of the exemplary scapular replacement device of FIG. 8A as fixed to a representative scapula.
Figure 9D:
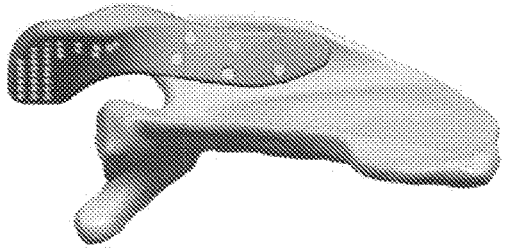
FIG. 9D shows an inferior view of the exemplary scapular replacement device of FIG. 8A as fixed to a representative scapula.
Figure 10A:
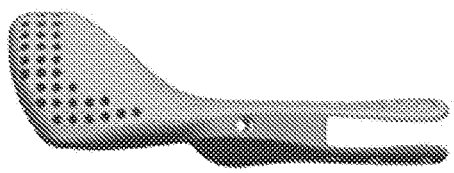
FIG. 10A shows a posterior view of a fourth exemplary embodiment of a scapular replacement device.
Figure 10B:
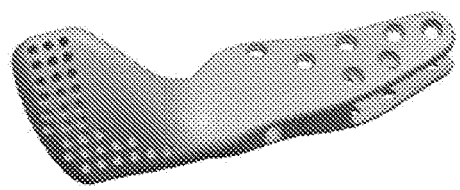
FIG. 10B shows a superior-oblique view of the exemplary scapular replacement device of FIG. 10A.
Figure 10C:
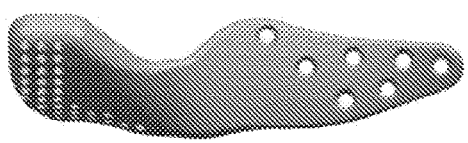
FIG. 10C shows a superior view of the exemplary scapular replacement device of FIG. 10A.
Figure 10D:
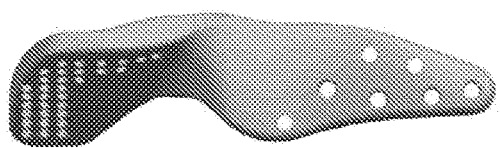
FIG. 10D shows an inferior view of the exemplary scapular replacement device of FIG. 10A.
Figure 11A:
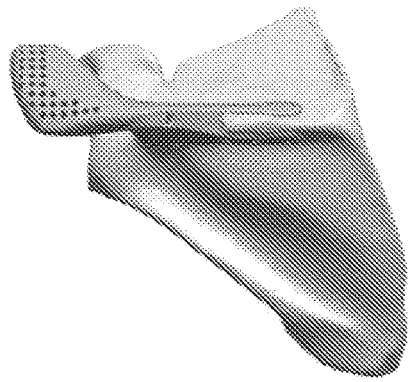
FIG. 11A shows a posterior view of the exemplary scapular replacement device of FIG. 10A as fixed to a representative scapula.
Figure 11B:
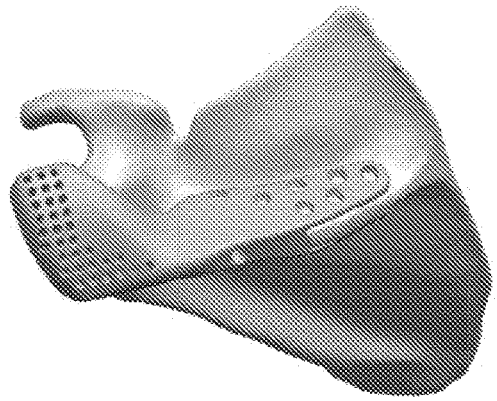
FIG. 11B shows a superior-oblique view of the exemplary scapular replacement device of FIG. 10A as fixed to a representative scapula.
Figure 11C:
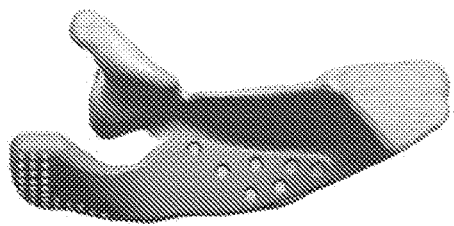
FIG. 11C shows a superior view of the exemplary scapular replacement device of FIG. 10A as fixed to a representative scapula.
Figure 11D:
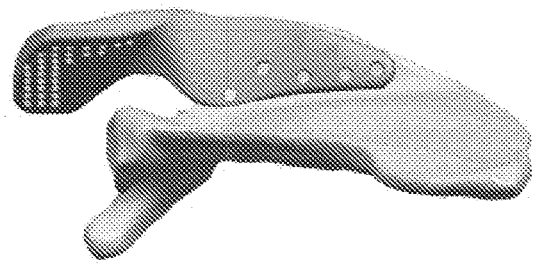
FIG. 11D shows an inferior view of the exemplary scapular replacement device of FIG. 10A as fixed to a representative scapula.
Figure 12A:
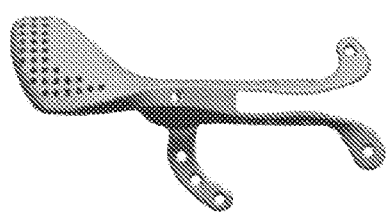
FIG. 12A shows a posterior view of a second exemplary embodiment of a scapular replacement device.
Figure 12B:
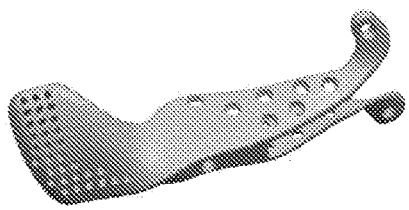
FIG. 12B shows a superior-oblique view of the exemplary scapular replacement device of FIG. 12A.
Figure 12C:
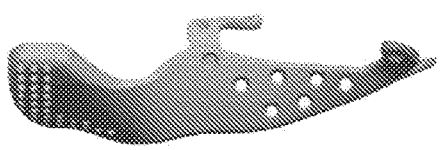
FIG. 12C shows a superior view of the exemplary scapular replacement device of FIG. 12A.
Figure 12D:
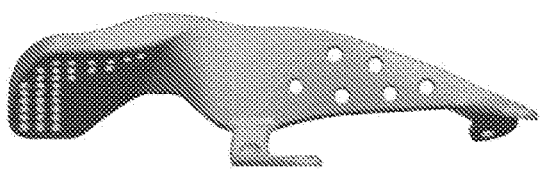
FIG. 12D shows an inferior view of the exemplary scapular replacement device of FIG. 12A.
Figure 13A:
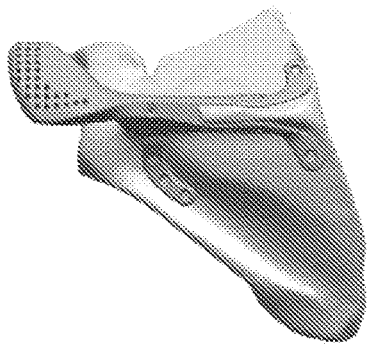
FIG. 13A shows a posterior view of the exemplary scapular replacement device of FIG. 12A as fixed to a representative scapula.
Figure 13B:
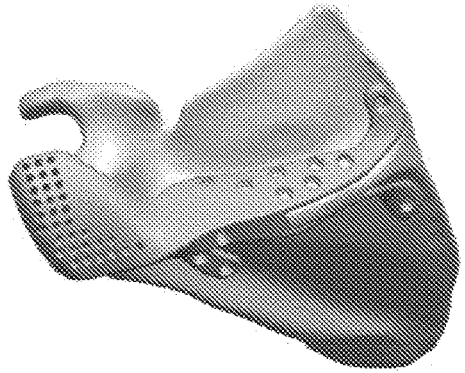
FIG. 13B shows a superior-oblique view of the exemplary scapular replacement device of FIG. 12A as fixed to a representative scapula.
Figure 13C:
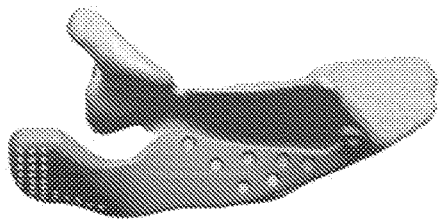
FIG. 13C shows a superior view of the exemplary scapular replacement device of FIG. 12A as fixed to a representative scapula.
Figure 13D:
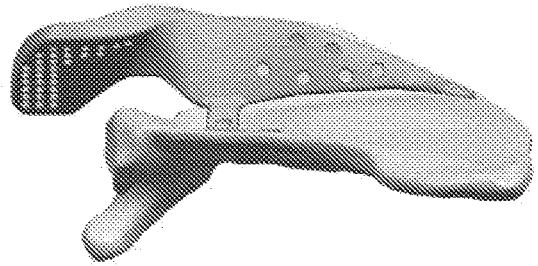
FIG. 13D shows an inferior view of the exemplary scapular replacement device of FIG. 12A as fixed to a representative scapula.

FIGS. 4A, 4B, and 4C show a superior-oblique view, a posterior view, and an inferior-oblique view, respectively, of an exemplary device. In some embodiments, an exemplary device includes fixation portion and an acromion portion projecting from the fixation portion. In some embodiments, the fixation portion has a "wishbone" type structure including a central portion and two arm portions projecting from the central portion. In some embodiments, the fixation portion lacks the central portion and the arm portions project from the acromion portion. In some embodiments, the central portion is configured to overlay the crest of the scapular spine. In some embodiments, the arm portions include a superior arm portion configured to overlay the superior face of the scapular spine and an inferior arm portion configured to overlay the inferior face of the scapular spine. In some embodiments, the fixation portion includes a plurality of screw holes through which screw or other fasteners can be passed so as to fix the device to the scapula. In some embodiments, the fixation portion includes at least one screw hole in the central portion. In some embodiments, the fixation portion includes at least one screw hole in the superior arm portion. In some embodiments, the fixation portion includes at least one screw hole in the inferior arm portion. In some embodiments, the acromion portion is configured (e.g., sized and shaped) to replace the native acromion. In some embodiments, the acromion portion includes at least one soft tissue attachment point (e.g., suture hole) configured to enable attachment of the deltoid so as to emulate the engagement of the deltoid with the native acromion. FIGS. 5A and 5B show a side view and a rear view, respectively, of the exemplary device of FIGS. 4A-4C as positioned on a representative scapula.

In some embodiments, exemplary devices are configured to restore stability to a shoulder with a fractured acromion and/or scapula by replacing the anatomic feature with metal with numerous features for soft tissue attachment of the deltoid and fixation to the scapula. In some embodiments, screw holes for screw fixation can be positioned to permit fusion of the clavicle to impart additional stability. In some embodiments, a peg is configured to secure in the clavicle from the anterior acromial tip, to impart additional stability. In some embodiments, an artificial scapular implant is configured to create additional stability via the use of a suture anchor or loop around the coracoid process for rigid fixation and to impart additional stability and functionally replicate the coracoid-acromial ligament. In some embodiments, the positions of the screw holes permit compression of the device to the fractured region of the scapula. In some embodiments, at least some of the suture holes are sized to allow needles of various sizes to easily pass therethrough. In some embodiments, the edges of the suture holes are configured so as not to abrade the attached soft tissue.

Figure 3C:
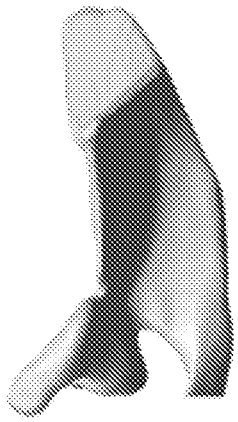
FIG. 3C shows a superior view of a scapula after a Type 1 fracture.
Figure 3D:
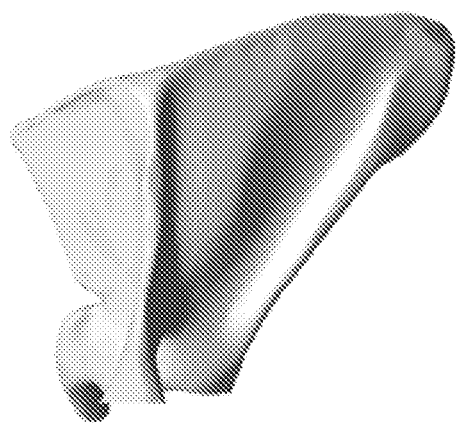
FIG. 3D shows a posterior view of the fractured scapula shown in FIG. 3C.
Figure 3A:
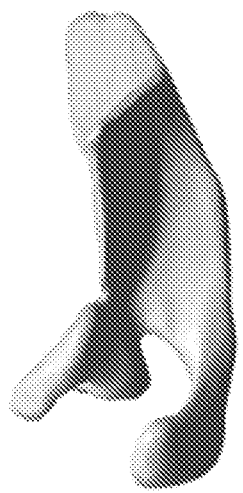
FIG. 3A shows a superior view of a healthy scapula.
Figure 3B:
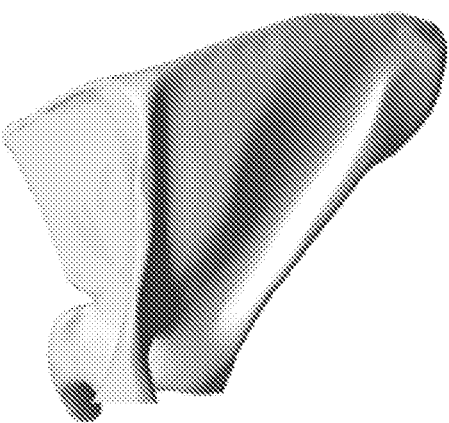
FIG. 3B shows a posterior view of the healthy scapula shown in FIG. 3A.

In some embodiments, exemplary devices are provided in multiple different sizes and shapes to account for the various fracture types that the orthopedic surgeon may be presented with. In some embodiments, exemplary devices are provided in different shapes for the different types of scapular fractures (i.e., type 1 fractures as shown in FIGS. 3C and 3D, type 2 fractures as shown in FIGS. 3E and 3F, and type 3 fractures as shown in FIGS. 3G and 3H) discussed above, each of which corresponds to a fracture at a different location within the scapula.

In some embodiments, a device is configured for repair of a type 1 fracture. FIGS. 6A-6D show a posterior view, a superior-oblique view, a superior view, and an inferior view, respectively, of an exemplary device that is configured for repair of a type 1 fracture (i.e., as shown in FIGS. 3C and 3D). In the embodiment shown in FIGS. 6A-6D, the fixation portion lacks a central portion and includes arm portions projecting from the acromion portion, and each of the arm portions includes a plurality of screw holes to facilitate fixation to the scapula. FIGS. 7A-7D show a posterior view, a superior-oblique view, a superior view, and an inferior view, respectively, of the device of FIGS. 6A-6D as fixed to a representative scapula that has experienced a type 1 fracture.

In some embodiments, a device is configured for repair of a type 2 fracture. FIGS. 8A-8D show a posterior view, a superior-oblique view, a superior view, and an inferior view, respectively, of an exemplary device that is configured for repair of a type 2 fracture (i.e., as shown in FIGS. 3E and 3F). In the embodiment shown in FIGS. 8A-8D, the fixation portion includes a central portion and arm portions projecting from the central portion, the central portion is small and lacks fixation screw holes, and each of the arm portions includes a plurality of screw holes to facilitate fixation to the scapula. FIGS. 9A-9D show a posterior view, a superior-oblique view, a superior view, and an inferior view, respectively, of the device of FIGS. 8A-8D as fixed to a representative scapula that has experienced a type 2 fracture.

In some embodiments, a device is configured for repair of a type 3 fracture. FIGS. 10A-10D show a posterior view, a superior-oblique view, a superior view, and an inferior view, respectively, of an exemplary device that is configured for repair of a type 3 fracture (i.e., as shown in FIGS. 3G and 3H). In the embodiment shown in FIGS. 10A-10D, the fixation portion includes a central portion and arm portions projecting from the central portion, the central portion is large (e.g., larger than the central portion of the embodiment shown in FIGS. 8A-8D) and includes a fixation screw hole, and each of the arm portions includes a plurality of screw holes to facilitate fixation to the scapula. FIGS. 11A-11D show a posterior view, a superior-oblique view, a superior view, and an inferior view, respectively, of the device of FIGS. 10A-10D as fixed to a representative scapula that has experienced a type 3 fracture.

In some embodiments, a device includes one or more extensions or shapes to provide multiple options for screw fixation into the scapula to gain increased fixation to the native bone. In some embodiments, such extensions are integrally formed with an exemplary scapular replacement device. In some embodiments, such extensions are modularly attachable to and removable from an exemplary scapular replacement device. In some embodiments, at least one such extension is configured to provide an option for screw fixation facing the superior scapular spine. In some embodiments, at least one such extension is configured to provide an option for screw fixation facing the inferior scapular spine. In some embodiments, at least one such extension is configured to provide an option for screw fixation adjacent to the medial border of the superior scapular spine. In some embodiments, at least one such extension is configured to provide an option for screw fixation adjacent to the medial border of the inferior scapular spine. FIGS. 12A-12D show a posterior view, a superior-oblique view, a superior view, and an inferior view, respectively, of an exemplary device that similar to the exemplary device shown in FIGS. 10A-10D (i.e., is configured for repair of a type 3 fracture), and also includes extensions providing additional locations for screw fixation into the scapula. In the embodiment, shown in FIGS. 12A-12D, extensions are included providing locations for screw fixation (a) adjacent to the medial border at a location of the superior scapular spine, (b) adjacent to the medial border at a location of the inferior scapular spine, and (c) inferior to the scapular spine. FIGS. 13A-13D show a posterior view, a superior-oblique view, a superior view, and an inferior view, respectively, of the device of FIGS. 12A-12D as fixed to a representative scapula that has experienced a type 3 fracture. It will be apparent to those of skill in the art that any other combination of extensions may be included in other exemplary embodiments. It will also be apparent to those of skill in the art that, while the embodiment of FIGS. 12A-12D is configured for repair of a type 3 fracture (i.e., as shown in FIGS. 3G and 3H), extensions such as those shown in FIGS. 12A-12D can also be incorporated into embodiments configured for repair of a type 1 fracture (i.e., as shown in FIGS. 3C and 3D) and/or into embodiments configured for repair of a type 2 fracture (i.e., as shown in FIGS. 3E and 3F). It will further be apparent to those of skill in the art that each such extension may include one screw hole for screw fixation, or may include more than one such screw hole.

It should be noted that any of the exemplary scapular replacement devices described above can be provided in a range of sizes and shapes to account for the normal anatomic variation in shapes and sizes present in the population and/or to permit better restoration of soft tissue stability when repairing the fracture (e.g., to permit the surgeon to provide more or less acromial overhang to lateralize or medialize the deltoid position differently, which may have positive biomechanical effects for the patient to encourage additional deltoid wrapping to impart stability, and/or to improve the length of the deltoid abduction moment arm or increase deltoid muscle tensioning). In some embodiments, the exemplary scapular replacement devices are manufactured to be bendable or conformable to facilitate additional patient-specific shaping to improve initial fixation when repairing to the scapula. In some embodiments, sutures, tape, anchors, or screws could also be used to fix the soft tissue to the scapular replacement. In some embodiments, screws are used to fuse the clavicle to help improve stability to the shoulder girdle. In some embodiments, the exemplary scapular replacement devices described above are manufactured from biocompatible materials, such as cobalt-chromium alloys, stainless steel, titanium, titanium alloys, nickel-titanium alloys, a polymer, a reinforced polymer (e.g., a carbon fiber-reinforced polymer, a glass-reinforced polymer, etc.), a non-reinforced polymer, ceramic, a polymethyl-methacrylate ("PMMA") such as bone cement, pyrocarbon, and/or bone graft.

In some embodiments, the exemplary scapular replacement devices described above are fabricated by traditional computer aided manufacturing processes, forged, cast, injection molded, or made by using additive manufacturing or similar processes. In some embodiments, the exemplary scapular replacement devices described above are designed in a patient-specific manner based upon the patient's actual anatomy (or contralateral anatomy) through the use of CT reconstruction and computer modeling. In some embodiments, the exemplary scapular replacement devices described above are surface coated or treated with various processes to encourage fixation to the soft tissue, muscle, and/or bone.

In some embodiments, an exemplary device is integrally formed from a metal plate that is cut and shaped to a desired size and shape. In some embodiments, the plate has a thickness in a range of between 3 mm and 10 mm. In some embodiments, the thickness is in a range of between 3 mm and 9 mm. In some embodiments, the thickness is in a range of between 3 mm and 8 mm. In some embodiments, the thickness is in a range of between 3 mm and 7 mm. In some embodiments, the thickness is in a range of between 3 mm and 6 mm. In some embodiments, the thickness is in a range of between 3 mm and 5 mm. In some embodiments, the thickness is in a range of between 3.5 mm and 4.5 mm. In some embodiments, the thickness is about 4 mm. In some embodiments, the thickness is 4 mm.

In some embodiments, the screw holes of an exemplary device have a diameter in range of between 1.0 mm and 4.5 mm. In some embodiments, the screw holes have a diameter in range of between 1.5 mm and 4.0 mm. In some embodiments, the screw holes have a diameter in range of between 2.0 mm and 3.5 mm. In some embodiments, the screw holes have a diameter in range of between 2.5 mm and 3.0 mm. In some embodiments, the screw holes have a diameter in range of between 1.0 mm and 4.0 mm. In some embodiments, the screw holes have a diameter in range of between 1.0 mm and 3.5 mm. In some embodiments, the screw holes have a diameter in range of between 1.0 mm and 3.0 mm. In some embodiments, the screw holes have a diameter in range of between 1.0 mm and 2.5 mm. In some embodiments, the screw holes have a diameter in range of between 1.0 mm and 2.0 mm. In some embodiments, the screw holes have a diameter in range of between 1.0 mm and 1.5 mm. In some embodiments, the screw holes have a diameter in range of between 1.5 mm and 4.5 mm. In some embodiments, the screw holes have a diameter in range of between 2.0 mm and 4.5 mm. In some embodiments, the screw holes have a diameter in range of between 2.5 mm and 4.5 mm. In some embodiments, the screw holes have a diameter in range of between 3.0 mm and 4.5 mm. In some embodiments, the screw holes have a diameter in range of between 3.5 mm and 4.5 mm. In some embodiments, the screw holes have a diameter in range of between 4.0 mm and 4.5 mm.

In some embodiments, an exemplary device includes one or more screw slots or compression slotted holes (e.g., as shown in FIGS. 4A-4C) configured to assist with fracture compression and fixation. In some embodiments, the screw slots or compression slotted holes have a length in a range of between 1 mm and 10 mm and a width in a range of 1 mm to 4.5 mm. In some embodiments, the screw slots or compression slotted holes have a length in a range of between 1 mm and 7 mm and a width in a range of 1 mm to 4.5 mm. In some embodiments, the screw slots or compression slotted holes have a length in a range of between 1 mm and 4 mm and a width in a range of 1 mm to 3 mm. In some embodiments, the screw slots or compression slotted holes have a length in a range of between 4 mm and 10 mm and a width in a range of 1 mm to 4.5 mm. In some embodiments, the screw slots or compression slotted holes have a length in a range of between 4 mm and 7 mm and a width in a range of 1 mm to 4.5 mm. In some embodiments, the screw slots or compression slotted holes have a length in a range of between 7 mm and 10 mm and a width in a range of 1 mm to 4.5 mm.

The term "screw fixation point" is used herein as a generic term to encompass screw holes, screw slots, and compression slotted holes.

In some embodiments, in areas of the device where the screw holes are present, the screw holes may be spaced apart from one another by a spacing distance (i.e., as measured from center to center or from edge to edge). In some embodiments, the spacing distance is between 1.0 cm and 4.0 cm. In some embodiments, the spacing distance is between 1.5 cm and 3.5 cm. In some embodiments, the spacing distance is between 2.0 cm and 3.0 cm. In some embodiments, the spacing distance is between 2.5 cm and 3.5 cm. In some embodiments, the spacing distance is between 1.0 cm and 3.5 cm. In some embodiments, the spacing distance is between 1.0 cm and 3.0 cm. In some embodiments, the spacing distance is between 1.0 cm and 2.5 cm. In some embodiments, the spacing distance is between 1.0 cm and 2.0 cm. In some embodiments, the spacing distance is between 1.0 cm and 1.5 cm. In some embodiments, the spacing distance is between 1.5 cm and 4.0 cm. In some embodiments, the spacing distance is between 2.0 cm and 4.0 cm. In some embodiments, the spacing distance is between 2.5 cm and 4.0 cm. In some embodiments, the spacing distance is between 3.0 cm and 4.0 cm. In some embodiments, the spacing distance is between 3.5 cm and 4.0 cm.

In some embodiments, the soft tissue attachment points of an exemplary device have a size (e.g., diameter, length, etc.) in range of between 5 mm and 50 mm. In some embodiments, the soft tissue attachment points have a size in range of between 10 mm and 45 mm. In some embodiments, the soft tissue attachment points have a size in range of between 15 mm and 40 mm. In some embodiments, the soft tissue attachment points have a size in range of between 20 mm and 35 mm. In some embodiments, the soft tissue attachment points have a size in range of between 25 mm and 30 mm. In some embodiments, the soft tissue attachment points have a size in range of between 5 mm and 45 mm. In some embodiments, the soft tissue attachment points have a size in range of between 5 mm and 40 mm. In some embodiments, the soft tissue attachment points have a size in range of between 5 mm and 35 mm. In some embodiments, the soft tissue attachment points have a size in range of between 5 mm and 30 mm. In some embodiments, the soft tissue attachment points have a size in range of between 5 mm and 25 mm. In some embodiments, the soft tissue attachment points have a size in range of between 5 mm and 20 mm. In some embodiments, the soft tissue attachment points have a size in range of between 5 mm and 15 mm. In some embodiments, the soft tissue attachment points have a size in range of between 5 mm and 10 mm. In some embodiments, the soft tissue attachment points have a size in range of between 10 mm and 50 mm. In some embodiments, the soft tissue attachment points have a size in range of between 15 mm and 50 mm. In some embodiments, the soft tissue attachment points have a size in range of between 20 mm and 50 mm. In some embodiments, the soft tissue attachment points have a size in range of between 25 mm and 50 mm. In some embodiments, the soft tissue attachment points have a size in range of between 30 mm and 50 mm. In some embodiments, the soft tissue attachment points have a size in range of between 35 mm and 50 mm. In some embodiments, the soft tissue attachment points have a size in range of between 40 mm and 50 mm. In some embodiments, the soft tissue attachment points have a size in range of between 45 mm and 50 mm.

The exemplary embodiments of a device described above with reference to FIGS. 4A-13D each include an acromion portion that both replicates the size and shape of, and is configured to replicate the functions of, a patient's native acromion. For example, it will be known to those of skill in the art that the native acromion acts as an attachment point for the deltoid muscle (in cooperation with the spine of the scapula and the clavicle) and for the trapezius muscle, which inserts on the acromion and the spine of the scapula, and forms the acromioclavicular joint in cooperation with the patient's native clavicle. In other embodiments, an exemplary device includes an acromion portion that replicates the function of the patient's native acromion (e.g., includes soft tissue attachment points suitable for attachment to the deltoid and the trapezius and to the acromioclavicular ligament to thereby form the acromioclavicular joint), but does not entirely replicate the size and shape of the native acromion (e.g., the shape of the portion of the device that is located between the soft tissue attachment points and the arms that facilitate fixation to the scapula may differ from the shape of the corresponding portion of the native acromion).

In some embodiments, the soft tissue attachment points are continuously located along the acromion and scapular spine to provide for attachment to the deltoid. In some embodiments, the soft tissue attachment points are separated by a distance of between 1 cm and 10 cm. In some embodiments, the soft tissue attachment points include suture holes, surface coatings, elongated (e.g., oblong) regions having rounded areas to permit multiple attachments.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A device,
   wherein the device is configured to replace an absent native acromion of a scapula of a patient,
   wherein the device comprises:
      an acromion portion sufficiently sized and shaped to replicate functions of the native acromion, and
      a fixation portion connected to the acromion portion, the fixation portion comprising a first arm portion and a second arm portion spaced apart from the first arm portion,
         wherein the first arm portion is positioned with respect to the acromion portion so as to be configured such that, when the device is positioned adjacent to the scapula such that the acromion portion is in a native position of the absent native acromion, the first arm portion overlays a superior face of a scapular spine of the scapula, and
         wherein the second arm portion is spaced apart from the first arm portion so as to be configured such that, when the device is positioned such that the first arm portion overlays the superior face of the scapular spine of the scapula, the second arm portion overlays an inferior face of the scapular spine of the scapula,
         wherein each of the first arm portion and the second arm portion includes at least one screw fixation point extending therethrough, wherein each of the at least one screw fixation point is configured to receive a screw therein so as to secure the device to the scapula.

2. The device of claim 1, wherein the fixation portion further comprises a middle portion connecting the acromion portion to the first arm portion and to the second arm portion, wherein the middle portion is positioned so as to be configured such that, when the device is positioned such that the first arm portion overlays the superior face of the scapular spine of the scapula, the middle portion overlays a crest of the scapular spine of the scapula.

3. The device of claim 2, wherein the middle portion includes at least one screw fixation point extending therethrough.

4. The device of claim 1, wherein the acromion portion includes at least one soft tissue attachment point.

5. The device of claim 4, wherein the acromion portion includes an array of soft tissue attachment points.

6. The device of claim 4, wherein each of the at least one soft tissue attachment point has a size in a range of from 5 mm to 50 mm.

7. The device of claim 1, wherein each of the first arm portion and the second arm portion includes a plurality of the screw fixation points.

8. The device of claim 7, wherein the screw fixation points are arranged in at least one row.

9. The device of claim 7, wherein the screw fixation points are arranged in a triangle.

10. The device of claim 7, wherein a spacing distance between adjacent ones of the plurality of screw fixation points is between 1 centimeter and 4 centimeters.

11. The device of claim 1, further comprising at least one extension extending away from either the first arm portion, the second arm portion, or both, wherein each of the at least one extension includes at least one screw fixation point extending therethrough.

12. The device of claim 11, wherein at least one of the at least one extension extends away from either the first arm portion or the second arm portion at an end of the first arm portion or the second arm portion that is closest to the acromion portion.

13. The device of claim 11, wherein at least one of the at least one extension extends away from either the first arm portion or the second arm portion at an end of the first arm portion or the second arm portion that is furthest from the acromion portion.

14. The device of claim 11, wherein the at least one extension is modularly attached to and removable from the device.

15. The device of claim 1, wherein the device is integrally formed.

16. The device of claim 1, wherein the device comprises a biocompatible material.

17. The device of claim 16, wherein the biocompatible material includes a cobalt-chromium alloy, stainless steel, titanium, a titanium alloy, a nickel-titanium alloy, a polymer, a reinforced polymer, a carbon fiber-reinforced polymer, a glass-reinforced polymer, a non-reinforced polymer, a ceramic, a polymethyl-methacrylate, bone cement, pyrocarbon, bone graft, or a combination thereof.

18. The device of claim 1, wherein the acromion portion is sized and shaped to replace an absent acromion of the scapula that has experienced either a type 1 fracture, a type 2 fracture, or a type 3 fracture.

19. The device of claim 1, wherein the acromion portion is sized and shaped to replicate a size and shape of the native acromion.

20. The device of claim 1, wherein each of the at least one screw fixation point includes either a screw hole, a screw slot, or a compression slotted hole.

21. A method, comprising:
providing the device as recited in claim 1;
positioning the device adjacent to a scapula of a patient that has experienced a fracture of the scapula causing the native acromion to be absent, such that the acromion portion of the device is positioned in a position that would be occupied by the native acromion; and
securing the device to the scapula by inserting at least one screw through the screw fixation points of the device and into the scapula.

22. The method of claim 21, wherein the acromion portion of the device includes at least one soft tissue attachment point, and wherein the method further comprises:
securing at least one of a deltoid of the patient or a trapezius of the patient to at least one of the at least one soft tissue attachment point.

* * * * *